United States Patent

Viccaro et al.

[11] Patent Number: 5,188,822
[45] Date of Patent: Feb. 23, 1993

[54] ORAL COMPOSITIONS CONTAINING AN AMINOSILICONE AND A LIPOPHILIC COMPOUND

[75] Inventors: John P. Viccaro, Whitestone, N.Y.; John S. Bajor, Cliffside Park; Alla Tartakovsky, West Orange, both of N.J.

[73] Assignee: Chesebrough-Pond's USA Co., Division of Conopco Inc., Greenwich, Conn.

[21] Appl. No.: 741,697

[22] Filed: Aug. 7, 1991

[51] Int. Cl.$^5$ .................... A61K 7/18; A61K 31/695; A01N 55/00
[52] U.S. Cl. ........................ 424/52; 424/54; 424/643; 424/55; 424/53; 424/405; 574/63
[58] Field of Search .................. 424/49, 52, 53, 54, 424/55; 574/63

[56] References Cited

U.S. PATENT DOCUMENTS

| 2,806,814 | 9/1957 | Richter | 424/49 |
|---|---|---|---|
| 3,507,955 | 4/1970 | Osipow | 424/54 |
| 3,794,736 | 2/1974 | Abbott et al. | 424/78 |
| 3,852,075 | 12/1974 | Basadur | 106/11 |
| 3,860,709 | 1/1975 | Abbott et al. | 424/184 |
| 4,161,518 | 7/1979 | Wen et al. | 424/52 |
| 4,243,658 | 1/1981 | Chang | 424/52 |
| 4,304,766 | 2/1981 | Chang | 424/52 |
| 4,465,661 | 8/1984 | Schmolka | 424/49 |
| 4,485,090 | 11/1984 | Chang | 424/52 |
| 4,510,127 | 4/1985 | Chang | 424/52 |
| 4,837,007 | 6/1989 | Duckworth et al. | 424/52 |
| 4,950,479 | 8/1990 | Hill et al. | 424/49 |
| 4,994,593 | 2/1991 | Lin et al. | 556/424 |
| 5,057,306 | 10/1991 | Hill et al. | 424/49 |
| 5,057,307 | 10/1991 | Hill et al. | 424/49 |
| 5,057,308 | 10/1991 | Hill et al. | 424/52 |
| 5,057,309 | 10/1991 | Hill et al. | 424/52 |
| 5,057,310 | 10/1991 | Hill et al. | 424/52 |

FOREIGN PATENT DOCUMENTS 686429 1/1953 United Kingdom .
689679 4/1953 United Kingdom .

OTHER PUBLICATIONS

Abstract of WO9113608.

Primary Examiner—Thurman K. Page
Assistant Examiner—Neil Levy
Attorney, Agent, or Firm—Rimma Mitelman

[57] ABSTRACT

Oral composition containing an oil-in-water emulsion, wherein the oil phase of the emulsion includes an aminoalkyl silicone and a lipophilic compound and the aqueous phase includes an emulsifier. The lipophilic compound is soluble in the aminoalkyl silicone. Preferably, a lipophilic antimicrobial agent or a lipophilic flavorant is employed. The aminoalkyl silicone forms a substantive film on the teeth surface and the lipophilic compound is deposited, along with the aminoalkyl silicone, on the teeth surface. Thus, the enhanced deposition of the lipophilic compound is attained. The pH of the compositions is preferably at least 7.0. The compositions are preferably applied by brushing.

24 Claims, No Drawings

ORAL COMPOSITIONS CONTAINING AN AMINOSILICONE AND A LIPOPHILIC COMPOUND

BACKGROUND OF THE INVENTION

1. Field of the Invention

The invention relates to oral compositions, particularly to oral compositions containing an aminosilicone and a lipophilic compound.

2. Related Art

Plaque is initiated when bacteria adhered to pellicle form a proteinaceous film on the surface of teeth. The adherent bacteria metabolize dietary constituents and produce and aggregate to form the tenatious deposit known as plaque. Plaque generally consists of bacteria, bacterial end products such as polysaccharides, inorganic salts and salivary proteins. Plaque bacteria ferment dietary carbohydrates to organic acids which demineralize enamel resulting in tooth decay.

Calculus is essentially plaque that has been mineralized with calcium phosphates salts. As calculus matures and hardens, it tends to stain noticeably due to adsorption of dietary chromagens. In addition to their unattractive appearance, calculus deposits at the gum line are a contributing source of gingivitis and periodontal disease. Besides the hygienic and health problems resulting from plaque, research has shown that the primary source of bad breath is the retention and subsequent degradation of dead cellular material sloughed off continuously by the normal, healthy mouth.

Modern dental hygiene preparations typically contain antiplaque and/or antitartar agents, as well as antimicrobial agents and flavorants. Antimicrobial action could affect plaque formation by either reducing the number of bacteria in the mouth or by killing those bacteria trapped in the film to prevent further growth and metabolism. Flavorants may alleviate the problem of bad breath via a deodorizing action. Some antimicrobial agents, e.g. menthol may, also serve as breath deodorizers. However, the efficacy of antimicrobial agents depends largely on their intraoral retention, particularly their retention on the tooth surface where plaque and calculus are formed.

A typical disadvantage of known dental preparations is that only a relatively short time during which the teeth are being cleaned or the mouth is being rinsed is available for antimicrobial agents in the preparations to take effect. The problem is compounded by the fact that dentifrice preparations are used infrequently: most are used once or, perhaps, twice daily. Consequently, the long time period between brushings for a majority of the population provides optimum plaque forming conditions.

There has been a need, therefore, for developing an oral formulation which has a prolonged, residual effect.

It is known to include silicones in dentifrice compositions. It has been proposed in the art that silicones would coat teeth and thereby prevent cavities and staining. For instance, British patent specification 689,679 discloses a mouthwash containing an organopolysiloxane for the purpose of preventing adhesion of, or for removal of, tars, stains, tartar and food particles from the teeth. The mouthwash may include antiseptic compounds, such as thymol, and flavoring and perfuming agents. The mouthwash may be prepared by mixing the polysiloxane, alcohol and emulsifying agent, adding an antiseptic, and, subsequently, diluting the mixture with water.

U.S. Pat. No. 2,806,814 (Richter) discloses dental preparations including, in combination, a higher aliphatic acyl amide of an amino carboxylic acid compound as an active and a silicone compound. The patent notes that silicone compounds have been proposed for prevention of adhesion or to facilitate the removal of tars, stains, tartar and the like from teeth. The patent also claims that the silicone compound acts as a synergist in improving the antibacterial and acid inhibiting activity of the active ingredient. Dimethyl polysiloxanes are said to have been found to be particularly effective in the Richter invention. Flavoring oils and/or menthol may be included.

However, silicone polymers such as those disclosed in the '679 specification and in the Richter patent, have not generally been successfully used for coating the teeth since it has been found that the polysiloxane does not adhere to the teeth for a prolonged period of time.

Viccaro et al., copending application Ser. No. 07/276 704 filed Nov. 28, 1988 and entitled "Dentifrices Containing Aminoalkyl Silicones", discloses Dentifrice Formulations including aminoalkyl silicones for coating the teeth and inhibiting stain and caries. The '704 application demonstrates that amino-functional groups increase the substantivity of silicone based polymers, apparently due to the interaction of the positively charged nitrogen of the amine with the negative charges on the surface of the teeth. Example I of the '704 application illustrates that aminoalkyl silicones are more substantive to a pellicle-coated surface than dimethicones. The antistaining properties of the dentifrices are said to be of particular significance when the aminoalkyl silicones are used in conjunction with antimicrobials such as quaternary salts or bis biguanides such as chlorhexidine digluconate.

Although the compositions of the '704 application may contain an antimicrobial agent, the specific antimicrobial agents disclosed therein (i.e. quaternary ammonium compounds or a bis biguanide such as chlorhexidine digluconate) are water-soluble. By contrast, antimicrobials included in the present invention are lipophilic. Further in contrast to the present invention, the '704 application does not teach the presence of any lipophilic compound or any antimicrobial compound, along with an aminoalkyl silicone, in an oil phase of oil-in-water emulsions. The '704 application expresses the belief that the aminoalkyl silicones prevent the adhesion of staining materials such as chlorhexidine digluconate and, additionally, facilitate removal of the staining materials from the teeth. By contrast, the aminoalkyl silicones in the present invention are employed to enhance the adhesion of lipophilic compounds to the teeth surface.

U.S. Pat. No. 4,994,593 (Lin et al.) discloses a specific class of modified aminosilicones which have reduced reactivity but still retain positive charges over a broad pH range. The Lin et al. patent also embraces compositions employing the modified aminosilicones. Lin et al. teach that dentifrices which include their aminoalkyl silicones can be used to form a hydrophobic barrier on the surface of teeth which is used for prevention of staining of teeth and in preventing cavities. Like in the '704 application, the antistaining properties of dentifrices incorporating the modified aminosilicones of the Lin et al. patent are said to be of particular significance when the compounds of the patent are used in conjunction with an antimicrobial quaternary ammonium salt or biguanide such as chlorhexidine digluconate. Lin et al. teach that increasing the number of aminoalkyl groups per molecule enhances the substantivity of the silicone. Also, increasing the charge density improves substantivity as well. Dentifrices including the modified aminoalkyl silicones of the Lin et al. patent are disclosed in a greater detail in Lin et al. copending application, Ser. No. 07/276,719, filed Nov. 28, 1988, now U.S. Pat. No. 5,078,988.

U.S. Pat. No. 4,243,658, U.S. Pat. No. 4,304,766, U.S. Pat. No. 4,485,090, and U.S. Pat. No. 4,510,127 (all authored by Chang) disclose a dentifrice composition for substantially reducing elution of a previously applied therapeutic agent from teeth. The composition contains at least 0.05% by weight, preferably from about 0.1 to 5%, of a membrane-forming material which, when applied to the surface of teeth in an oral environment, forms a substantially continuous hydrophobic barrier thereon which substantially reduces the elution of the previously applied therapeutic agent from the tooth. The membrane-forming material may be polymeric or nonpolymeric, ionic or nonionic. The nonionic material may be represented by the formula $[R^8]_b$-Si-$[R^9]_{4-b}$, where $R^8$ may be a hydrocarbon group and may contain heteroatoms selected from nitrogen, sulfur, oxygen, and silicon; $R^9$ is an alkoxy group containing from 1 to 6, and preferably from 1 to 3, carbon atoms; the value of b is 0, 1, 2 or 3. The only therapeutic agents disclosed by the Chang patents are fluoride salts; these are applied prior to the application of the membrane-forming material. The Chang patents do not appear to suggest that any silicones or any aminoalkyl silicones may be employed to enhance the deposition of a lipophilic compound on the teeth surface. Likewise, the Chang patents do not suggest the co-presence of any silicone and lipophilic compounds in an oil phase of oil-in-water-emulsions.

Thus, the related art discussed above does not provide any oral compositions which include an aminoalkyl silicone and a lipophilic compound in the oil phase of oil-in-water emulsions, or which provide an enhanced deposition of a lipophilic compound on the teeth surface, or which effectively prolong the action of a lipophilic compound in the mouth.

Accordingly, it is an object of the invention to provide oral compositions containing an oil-in-water emulsion, the emulsion including an aminoalkyl silicone and a lipophilic compound in an oil phase and an emulsifier in an aqueous phase.

It is another object of the invention to provide oral compositions containing an oil-in-water emulsion, wherein the emulsion includes an aminoalkyl silicone and a lipophilic antimicrobial in the oil phase and an emulsifier in the aqueous phase.

It is yet another object of the invention to provide oral compositions containing an oil-in-water emulsion, wherein the emulsion includes an aminoalkyl silicone and a lipophilic flavoring or perfuming agent in the oil phase and an emulsifier in the aqueous phase.

It is still another object of the invention to provide a method of preparing an oral composition containing an oil-in-water emulsion, the emulsion including an aminoalkyl silicone and a lipophilic compound in an oil phase and an emulsifier in an aqueous phase.

It is still another object of the invention to provide a method of delivering a lipophilic compound to the teeth surface by applying into an oral cavity a composition containing an oil-in-water emulsion, the emulsion including an aminoalkyl silicone and a lipophilic compound in an oil phase and an emulsifier in an aqueous phase.

These and other objects of the invention will become more apparent from the detailed description and examples which follow.

SUMMARY OF THE INVENTION

The invention includes oral compositions containing an oil-in-water emulsion, wherein the aqueous phase of the emulsion contains an emulsifier and wherein the oil phase includes a noncyclic, hydrophobic aminoalkyl silicone and an orally acceptable lipophilic compound which is soluble in the aminoalkyl silicone. The invention is based, in part, on the discovery that a compound, which is lipohilic and is soluble in aminoalkyl silicone can be delivered and imparted, along with the aminoalkyl silicone, to the teeth surface. The aminoalkyl silicone forms a residual film on the surface of teeth. Since, according to the invention, a lipophilic compound forms a part of the film, the retention of the lipophilic compound on the teeth surface is improved and the effect of the lipophilic compound in the mouth is prolonged and enhanced. The invention is useful whenever it is desired to deliver any orally acceptable lipophilic compound to the teeth surface. According to the present invention, the deposition on the teeth surface of any lipophilic agent employed in oral compositions can be enhanced/prolonged.

In one preferred embodiment of the invention, a lipophilic compound is an antimicrobial compound, e.g., thymol. In such embodiment, when the inventive composition is applied to teeth, a substantive antimicrobial film is imparted to the teeth surface.

In another preferred embodiment of the invention, a lipophilic compound is a flavorant and the inventive compositions, upon application to the teeth surface, effectively provide a prolonged release of the flavorant. In this embodiment, the inventive compositions provide a prolonged flavor perception and/or a sustained breath refreshing benefit and/or masking malodors. Some lipophilic compounds, e.g. menthol, provide both an antimicrobial and a breath refreshing benefit.

The invention also includes a process for manufacturing the inventive compositions and a method of delivering a lipophilic compound to the teeth surface.

The compositions of the present invention may be incorporated in toothpaste creams, or gels, or mouthwashes. The compositions may also be incorporated into chewing gums, dentifrice spray, measured drops, masticatable capsules and the like.

The inventive compositions may constitute an integral part of a toothpaste cream or gel, or mouthwash and may be applied during the regular brushing, or the compositions may be formulated and packaged as a separate treatment and applied separately before, after, and/or in between regular brushing times.

DETAILED DESCRIPTION OF THE INVENTION

Unless otherwise specified or required by the context, percentages of ingredients are by weight of the final composition.

Compositions according to the present invention include a noncyclic hydrophobic aminoalkyl silicone as an essential ingredient. The aminoalkyl silicones form a hydrophobic layer on the surface of teeth. In a preferred embodiment, the aminoalkyl silicones comprise amodimethicones. Amodimethicones are polydimethyl siloxane polymers containing aminoalkyl groups. The aminoalkyl groups may be present either pendant or at one or more ends of the polydimethylsiloxane chain. Also preferred are aminoalkyl silicones having a molecular weight of about 5,000 and above.

The aminoalkyl silicone is included in the inventive compositions in the amount effective to form a hydrophobic layer on the teeth surface. The compositions of the invention preferably contain from 0.1% to 20% by weight, more preferably from 0.1 to 10% by weight, most preferably from 0.5 to 5% of the aminoalkyl silicones. The aminoalkyl silicones employed herein are non-cyclic and hydrophobic. The preferred aminoalkyl silicones include two basic units of formulas 1 and 2. The aminoalkyl silicones may be linear, branched, random or block copolymers. Formulas 1 and 2 are as follows:

$$(R^1)_m(R)_n SiO_{(4-m-n)/2} \quad (1)$$

wherein
$1 \leq m+n \leq 3$,
$1 \leq n \leq 3$,
$0 \leq m \leq 2$, where m and n are integers, preferably
m=2,
n=1
and $$(R^1)_a(R^2)_b SiO_{(4-a-b)/2} \quad (2)$$

wherein $1 \leq a+b \leq 3$, and a and b are integers, and wherein $R^1$ and $R^2$ are preferably hydrocarbons or fluorinated hydrocarbons of 1 to 10, even more preferably 1 to 4 carbon atoms. Examples include methyl, ethyl, phenyl, vinyl, trifluoropropyl and -cyanopropyl. Methyl and phenyl are preferred. $R^1$ and $R^2$ may also be hydroxyl, alkoxy, hydrogen, acetoxy or other reactive groups but their amounts are preferred to be low in order to promote adequate shelf stability.

The value of (4-m-n)/2 in Formula 1 and/or (4-a-b)/2 in Formula 2 means the ratio of oxygen atoms to silicon atoms, i.e. $SiO_{1/2}$ means one oxygen is shared between two silicon atoms.

R is defined as

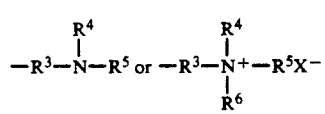

wherein $R^3$ is a divalent alkylene of 1 to 20 carbons, optionally including O atoms, preferably 3 to 5 carbons. $R^4$, $R^5$ and $R^6$ may be different or the same and are H, hydrocarbons of 1 to 20 carbons, and hydrocarbons of 1 to 20 carbons containing N and/or O atoms. $R^4$, $R^5$ and $R^6$ preferably contain 1 to 10, even more preferably 1 to 4 carbon atoms. Examples are methyl, ethyl and phenyl. $X^-$ is an anion preferably selected from the group consisting of halide, hydroxide, tosylate and other monovalent anions. Examples of R include:

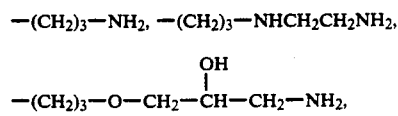

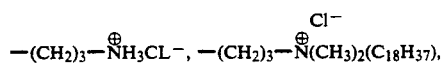

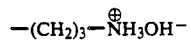

and $-(CH_2)_3-N(CH_2CH_2OH)_2$.

The concentration of formula (1) in the aminoalkyl silicone may range from 1 to 99% by repeat units, preferably from 1 to 60%, more preferably from 5 to 30%, and even more preferably from 5 to 10%. The preferred minimum molecular weight of the aminoalkyl silicone of the invention is 5,000. It is desirable that the molecular weight of the aminosilicones compounds be about 5,000 or greater since at molecular weights below 5,000 cyclization may occur and the compounds may dissolve in water. It is believed important that the silicones not be cyclized and not be soluble in order to permit them to deposit a lasting film onto the teeth. If the aminosilicones are unduly soluble in water, it is believed that the film will too readily wash off the teeth.

There is no theoretical ceiling on the molecular weights of the silicones so long as they spread onto tooth enamel by brushing or chewing action or rinsing. Molecular weights will tend to fall within the range of 5,000 to 100,000, preferably 5,000 to 30,000. However, molecular weights may range as high as 1,000,000 or more. Particularly preferred are compositions having average molecular weights of aminoalkyl silicones in the ranges above. Silicones of high and low molecular weights may be mixed together to obtain mixtures of the desired viscosity. A viscosity for the aminoalkyl silicone in the range of 50 cps to 3,000 cps is preferred.

In the preferred embodiment the composition preferably comprises an oil-in-water emulsion which includes in an oil phase a mixture of:

(I) from 0.1 to 20% by weight, even more preferably from 0.1 to 10% by weight and most preferably from 0.5 to 5% by weight of an organosiloxane polymer which includes:

a) at least one unit of formula 3,

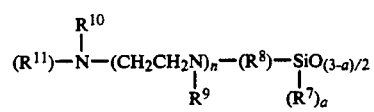

wherein
a is from 0–2 and n is from 0–5,
$R^7$ is a monovalent radical,
$R^8$ is a divalent hydrocarbon radical,
$R^9$, $R^{10}$ and $R^{11}$ may be the same or different and are selected from the group consisting of

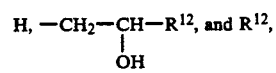

where
$R_{12}$ is a monovalent hydrocarbon radical or hydrogen, and
b) at least one unit of formula 4, $$(R^{13})_a(R^{14})_c\mathrm{SiO}_{(4-a-c)/2} \qquad (4)$$

wherein
$R^{13}$ and $R^{14}$ are the same or different monovalent radicals,
a and c are integers selected from the group of 0,1,2 and 3,
and a+c is 0, 1, 2 or 3, and (II) from 0.01 to 10%, more preferably from 0.05 to 5% by weight of an orally acceptable lipophilic compound, preferably a lipophilic antimicrobial compound or a lipophilic flavoring ingredient.

Each $R^7$ may independently be a hydrocarbon radical, a halogenated hydrocarbon radical, hydrogen, hydroxyl or alkenyl. Preferably, $R^7$ comprises from 1 to 10 and even 1 to 4 carbon atoms. Examples of $R^7$ are methyl, phenyl or -trifluoropropyl.

Each $R^8$ independently preferably comprises a divalent hydrocarbon radical having 3 or more carbons. Examples are propylene and butylene. Preferably, $R^8$ does not exceed 10 carbon atoms.

$R^{12}$ is preferably selected from the group consisting of hydrogen, methyl or phenyl. Preferably $R^{12}$ includes 10 or fewer carbon atoms, more preferably, 4 or fewer.

Preferably $R^{13}$ and $R^{14}$ are independently selected from the group consisting of hydrocarbon radicals, halogenated hydrocarbons, hydrogen, hydroxyl and alkoxyls. It is preferred that $R^{13}$ and $R^{14}$ include from 1 to 10, preferably from 1 to 4 carbon atoms. Especially preferred $R^{13}$ and $R^{14}$ groupings are independently selected from the group consisting of methyl, phenyl and -trifluoropropyl.

Preferably a+c is equal to 2.

For example, the organopolysiloxane polymer comprising at least one unit of Formula 3 and one unit of Formula 4 may be used in a composition according to the invention.

Examples of Formula 3 are:

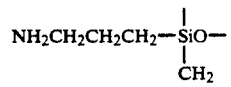

and

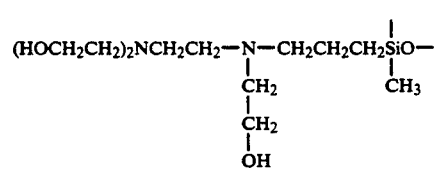

The content of Formula 3 in the polymer ranges from 0.5% and up to 60% by repeat unit, preferably between 1 and 30%, more preferably from 5 to 15% by repeat unit. For reasons given above, the molecular weight is preferably above about 5,000.

The molecular weight of the preferred compound is preferably between 5,000 and 100,000, preferably between 5,000 and 30,000, although it may be as high as 1,000,000 or more. An example of such a polysiloxane is as follows:

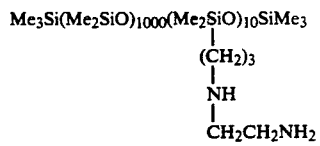

With the exception of the ethoxylated and propoxylated compounds discussed below, the aminoalkyl silicone compounds are, for the most part, known. Methods of preparing aminoalkyl silicones are given in, for example, Jex et al, U.S. Pat. No. 2,930,809, including U.S. application Ser. Nos. 555,201 (filed Dec. 23, 1955) and 555,203 (filed Dec. 23, 1955), all of which are hereby incorporated by reference.

The aminoalkyl polysiloxanes of the invention may be end capped. If end capped, one or more of the end capping groups, $R_e$, preferably includes one or more nitrogen atoms. For example, $R_e$ may be -(CH$_2$)$_3$NH$_2$ or —(CH$_2$)$_3$NHCH$_2$CH$_2$NH$_2$.

As indicated above, a preferred class of aminoalkyl polysiloxanes is that of the amodimethicones. Amodimethicones are polydimethyl siloxane polymers containing aminoalkyl groups. The aminoalkyl groups may be, for example, n-propylamine or n-propyl-N-ethylenediamine and these may be present either pendant or at one or more ends of the polydimethylsiloxane chain. The amine groups cause the amodimethicone polymer to develop a net positive charge in aqueous systems over a wide range of pH say from pH 1 to 10. Examples of amodimethicones include Dow Corning's DC-929, DC-Q2-7224 and Q2-8075. These polymers comprise aminoalkyl groups affixed to a predominantly polydimethylsiloxane structure. The typical structure of Q2-8075's aminoalkyl group-containing units is:

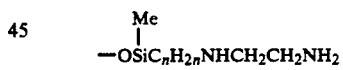

The amodimethicones most preferred in the present invention are exemplified by the formula which is shown in Formula 5 below:

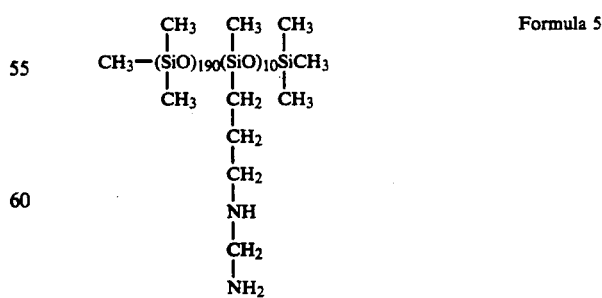

Formula 5

A special class of aminosilicones are ethoxylated and propoxylated aminosilicone compounds such as the following ethoxylated compound:

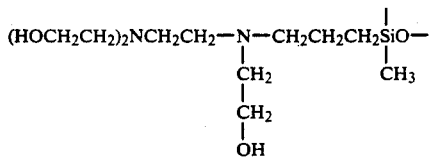

These have less of a tendency to react with aldehyde flavorants due to the presence of hydroxypropyl and hydroxyethyl groups. These compounds are described more fully in Lin et al., U.S. Pat. No. 4,994,593 and in Lin et al. application 07/276,719, now allowed, both of which are incorporated by reference hereby.

The substantivity of various dimethicones and amodimethicones as indicated in the table below has been investigated in the copending application Ser. No. 07/276,704. The % reduction in acid dissolution values in the table below demonstrates the improved effectiveness of amino-functional silicones over alkyl silicones in depositing onto an enamel surface and, thus, protecting it from caries.

| SILICONE POLYMER | MOLE-CULAR WEIGHT | % REDUCTION IN ACID DISSOLUTION | MOLE % ALKYL-AMINE |
|---|---|---|---|
| Dimethicones: | | | |
| Union Carbide LE-474 | 12,000 | 4.46 | 0.0 |
| LE-460 | 28,000 | 9.85 | 0.0 |
| SWS Silicones 100 cs | 6,600 | 15.0 | 0.0 |
| SWS Silicones 500 cs | 19,000 | 5.2 | 0.0 |
| Petrarch Sys. 1000 cs | 26,000 | 6.6 | 0.0 |
| Amodimethicones: | | | |
| End capped with methoxyl group | 12,000 | 27.3 | 2.5 |
| End capped with methoxyl group | 18,000 | 25.6 | 1.6 |
| End capped with hydroxyl group | — | 33.3 | Low |
| End capped, $R^1$ | 6,000 | 25.0 | 2.5 |
| | 15,000 | 21.3 | 1.0 |
| | 22,000 | 16.0 | 0.7 |
| End capped, $R^2$ | 19,000 | 24.2 | 0.8 |
| | 28,000 | 28.0 | 0.7 |
| Pendant, $R^1$ | 5,000 | 68.0 | 9.5 |
| | 15,000 | 47.9 | 3.0 |
| | 25,000 | 36.6 | 1.8 |
| Pendant, $R^2$ | 25,000 | 39.8 | 1.8 |
| Dow Corning (pendant amines hydroxyl end groups) | 929 | 25.7 | Low |
| Q2-7224 | — | 10.4 | 2.0 |
| Q2-8075 | — | 28.7 | 2.0 |
| Compound of Formula 5 | 15,000 | 53.0 | 5.0 |

$R^1$ = n-propylamine
$R^2$ = n-propyl-N-ethylenediamine
DIMETHICONE (POLYDIMETHYLSILOXANE)

$$CH_3-\underset{\underset{CH_3}{|}}{\overset{\overset{CH_3}{|}}{Si}}-\left[\underset{\underset{CH_3}{|}}{\overset{\overset{CH_3}{|}}{O-Si}}\right]_x -O-\underset{\underset{CH_3}{|}}{\overset{\overset{CH_3}{|}}{Si}}-CH_3$$

AMODIMETHICONES, END CAPPED $$R-\underset{\underset{CH_3}{|}}{\overset{\overset{CH_3}{|}}{Si}}-\left[\underset{\underset{CH_3}{|}}{\overset{\overset{CH_3}{|}}{O-Si}}\right]_x -O-\underset{\underset{CH_3}{|}}{\overset{\overset{CH_3}{|}}{Si}}-R$$

AMODIMETHICONE, PENDANT $$HC_3-\underset{\underset{CH_3}{|}}{\overset{\overset{CH_3}{|}}{Si}}-\left[\underset{\underset{CH_3}{|}}{\overset{\overset{CH_3}{|}}{O-Si}}\right]_x -\left[\underset{\underset{R}{|}}{\overset{\overset{CH_3}{|}}{O-Si}}\right]_y -O-\underset{\underset{CH_3}{|}}{\overset{\overset{CH_3}{|}}{Si}}-CH_3$$

For $R^1$, R = $CH_2CH_2CH_2NH_2$
For $R^2$, R = $CH_2CH_2CH_2NHCH_2CH_2NH_2$

As demonstrated by the results in the table above, there is a correlation between percent alkylamine in aminoalkyl silicone and the ability of the silicone to form a hydrophobic film.

In the silicones with methoxy end caps, the methoxy group may further lend to the polymer's attachment to enamel through a covalent linkage thereby increasing polymer substantivity. The DC-929 is a commercially available emulsion of a polyalkyl silicone having low pendant amine content and hydroxyl end groups. Hydroxyl end groups may also enhance deposition in a manner similar to that of the methoxyl groups.

As a class, aminoalkyl silicones are more substantive to enamel than dimethicones. The most substantive amino silicone polymers are those which possess more than 3% alkylamine, pendantly attached to the polydimethylsiloxane backbone.

The second essential ingredient of the inventive compositions is a lipophilic compound, which is included together with an aminoalkyl silicone in the oil phase of inventive compositions. A lipophilic compound, as defined herein, is a compound which dissolves in fatlike solvents. While the compounds suitable for use herein may have minimal solubility in water, their solubility in fatlike solvents is substantially greater. Generally, the solubility of a lipophilic compound in a fatlike solvent should be high enough to prepare at least 1% solution of the compound in the fatlike solvent. Further, the lipophilic compound should be soluble in the chosen aminoalkyl silicone. Preferably, the minimal solubility of the lipophilic compound in the aminoalkyl silicone is at least 0.01 g of the compound per 1 g of the silicone.

The lipophilic compound may be any lipophilic ingredient desirable in oral compositions as long as the compound satisfies the solubility requirements outlined above. The lipophilicity of the compound and its solubility in the aminoalkyl silicone are critical for attaining an enhanced deposition and a residual effect. The lipophilic compound is delivered and deposited, along with the aminoalkyl silicone, on the teeth surface.

In one preferred embodiment of the present invention the lipophilic compound is a lipophilic antimicrobial agent. Suitable antimicrobial agents include but are not limited to thymol, menthol, triclosan, (Irgasan DP300® ex Ciba-Geigy), 4-hexylresorcinol, phenol, eucalyptol, benzoic acid, benzoyl peroxide, butyl paraben, methyl paraben, propyl paraben, and mixtures thereof. Salicylamides (including salicylanilides and salicylanilides with halogens as substituents) are also lipophilic and may be suitably employed in the oil phase of the present emulsions. Coburn et al, U.S. Pat. Nos. 4,358,443 and 4,287,191 describe salicylamides and are incorporated by reference herein.

The lipophilic compound may also be a flavoring or perfuming agent, exemplified by such materials as wintergreen oil, oregano oil, bay leaf oil, peppermint oil, spearmint oil, clove oil, sage oil, sassafras oil, lemon oil, orange oil, anise oil, benzaldehyde, bitter almond oil, camphor, cedar leaf oil, marjoram oil, citronella oil, lavendar oil, mustard oil, pine oil, pine needle oil, rosemary oil, thyme oil, cinnamon leaf oil, and mixtures thereof as long as the above compounds are soluble in the aminoalkyl silicone.

Of course, other lipophilic compounds may be employed in the inventive compositions, as long as they are orally acceptable and satisfy the solubility requirements outlined above. Also, mixtures of lipophilic compounds may be employed.

The amount of the lipophilic compound in the present compositions typically ranges from 0.01 to 10% by weight, preferably from 0.05 to 5%, most preferably from 0.1 to 3%. Generally, no upper limit on the concentration of the lipophilic compound exists. It has been found that the increased concentration of the lipophilic compound in the oil phase leads to an increased deposition. However, once the concentration exceeds the solubility of the antimicrobial compound in the aminoalkyl silicone, no further deposition enhancement is observed.

When the lipophilic compound is a phenolic antimicrobial (e.g.,thymol or triclosan), preferably at least 0.05%, most preferably 0.1 to 3%, is included in the compositions in order to provide an antimicrobial benefit at an optimum cost. Salicylamides are typically employed in the amount of at least 0.01%, preferably from 0.05 to 3%, most preferably from 0.1 to 2%. When the lipophilic compound is a flavoring agent, the amount typically ranges from 0.01 to 5%, preferably from 0.1 to 3%. It should be noted that some lipophilic compounds, for instance menthol, may perform both an antimicrobial and a flavoring function.

The aqueous phase of the oil-in-water emulsion of the present compositions contains an emulsifier. Nonionic surfactants and/or cationic surfactants are preferred emulsifiers, although anionics such as sarcosinates may also be used. Surfactants must be orally acceptable.

Examples of suitable surfactants include but are not limited to:

(i) condensation products of ethylene oxide with various reactive hydrogen-containing compounds reactive therewith having long hydrophobic chains (e.g. aliphatic chains of about 12 to 20 carbon atoms, which condensation products contain hydrophilic polyoxyethylene moieties, such as condensation products of poly-(ethylene oxide) with fatty acids, fatty alcohols, fatty amides, polyhydric alcohols (e.g. sorbitan monostearate, sorbitan oleate), alkyl phenols (e.g. Tergito® materials, and polypropyleneoxide or polyoxybutylene (e.g. Pluronic® materials). Also included are the reaction products of ethylene oxide with long chain tertiary dialkyl sulfoxides.

(ii) amine oxides, such as decyl-N,N-dimethylamine oxide, lauryl-N,N-dimethylamine oxide, stearyl-N-N-dimethylamine oxide, oleyl-N,N dimethylamine oxide, coco-N,N-dihydroxyethylamine oxide, cetyl-N,N-dihydroxyethylamine N,N-dihydroxyethylamine oxide, oleyl-N,N-dihydroxyethylamine oxide, and mixtures of the same. Particularly preferred among amine oxides are dimethyl cocamine oxide, dimethyl lauryl amine oxide and cocoalkyldimethyl amine oxide (Aromox® materials from AKZO);

(iii) polysorbates, e.g., Tween 40® and Tween 80® (Hercules)

(iv) sorbitan stearates, sorbitan monoaleate, etc.

(v) sarcosinates, e.g. sodium cocoylsarcosinate, sodium lauroyl sarcosinate (Hamposyl-95® ex W. R. Grace)

(vi) cationic surfactants may be quaternary ammonium compounds including one $C_8$-$C_{18}$ alkyl chain. Examples include cetyl pyridinium chloride, cetyl trimethyl ammonium bromide, di-isobutyl phenoxy ethoxy ethyl-dimethyl benzyl ammonium chloride and coconut alkyl trimethyl ammonium nitrate Preferred surfactants are nonionic surfactants, for reasons of optimum performance, particularly polyoxypropylene-polyoxypropylene block copolymers and polyoxyethylene-polyoxybutylene block copolymers, such as Pluronic® materials (BASF), and polyoxyethylene derivatives of a fatty alcohol having 15 to 20 carbon atoms wherein the polyoxyethylene chains are responsible for about 50 to about 90% of the molecular weight of the surfactant (described in U.S. Pat. No. 4,465,661 incorporated by reference herein). Also preferred are amine oxides due to their good emulsifying performance.

Surfactants are present in an amount effective to emulsify the silicone/lipophilic compound mixture. The concentration of the surfactant varies depending on the particular identity of the surfactant. Generally, surfactants may be present within the range of from 0.05 to 10%, preferably in the range of from 0.1 to 5%, more preferably in the range of from 0.1 to 3% by weight.

The relative amounts of a lipophilic compound, an aminoalkyl silicone, and an emulsifier in the inventive compositions vary depending on the particular lipophilic compound, the particular aminoalkyl silicone and the degree of solubility of the lipophilic compound in the aminoalkyl silicone, and the stability of the resulting oil-in-water emulsion.

While not wishing to be bound by theory, it is believed that the delivery of the aminoalkyl silicone/lipophilic compound mixture to the teeth surface depends, in part, on the stability of the emulsion. It has been found that the deposition decreases when a microemulsion (an ultra-stable emulsion) is formed. It is believed that an increased amount of the emulsifier leads to a decreased droplet size of an aminoalkyl silicone, and may result in the formation of a microemulsion. It is believed that in an ultra-stable emulsion (or a microemulsion) it becomes harder for the silicone (and a lipophilic compound together with it) to separate from the aqueous phase in order to deposit on the teeth surface.

Thus, on one hand, the relative amounts of the aminoalkyl silicone, the lipophilic compound and the emulsifier are preferably such as to avoid the formation of a microemulsion, so that the aminoalkyl silicone/lipophilic compound mixture can easily leave the emulsion and deposit on the teeth surface upon the application of the inventive compositions to the surface.

On the other hand, the emulsions should be sufficiently stable so that the oil does not separate out on standing. This is particularly important for toothpaste formulations, where once the separation occurs, the emulsion cannot be formed again by shaking the composition. In this respect, it has been found that the addition of a thickening agent increases the stability of the emulsions preventing the separation of the oil phase, yet the deposition of the aminoalkyl silicone and the lipophilic compound is not adversely affected by the presence of the thickening agent. Thus, the compositions of the invention preferably include a thickening agent, preferably in an amount of from 0.01 to 10%. Thickening agents suitable for use in the compositions of the invention include hydroxyethyl cellulose (Natrosol ®), sodium carboxymethyl cellulose and hydroxypropyl cellulose (Klucel ®), as well as xanthan gums, silica, acacia Irish moss and gum tragacanth.

Preferably, the weight ratio of the lipophilic compound amount to the aminoalkyl silicone amount is in a range of from 1:10 to 1:2.

According to the present invention, the oil-in-water emulsions are prepared as follows. First, a mixture of an aminoalkyl silicone and a lipophilic compound is prepared. Although heating may not be necessary when low viscosity silicones are employed, generally the aminoalkyl silicone is heated, typically to about 30° to 80° C., most preferably to about 50°-70° C. If the aminoalkyl silicone is a solid or a highly viscous compound, it is melted. The desired amount of a lipophilic compound is added to the aminoalkyl silicone. The resulting mixture is stirred, typically by using an overhead mixer, until the lipophilic compound is dissolved in the aminoalkyl silicone. The resulting solution containing the aminoalkyl silicone and the lipophilic compound is then added, slowly, to an aqueous phase containing an emulsifier. The addition is carried out with stirring, preferably with high shear stirring, generally at 250 to 2,000 rpm, preferably at 500 to 1500 rpm. The stirring is continued until a visibly stable emulsion is formed, typically for about 10 to 90 minutes, preferably for about 10 to 30 minutes. Subsequently, thus obtained concentrated emulsion is diluted with water to yield a composition containing the desired amount of the aminoalkyl silicone. The composition is again subjected to high shear stirring for approximately 10 to 60 minutes, typically for about 30 minutes, to ensure proper emulsification.

Alternatively, a slightly different method may be employed, as follows. The aminoalkyl silicone/lipophilic compound mixture is prepared as described above. A slurry paste is then prepared containing approximately equal weights of an emulsifier and water, by stirring the water and the emulsifier, preferably with an overhead stirrer. Subsequently, the silicone/lipophilic compound mixture is added slowly (over 30 minutes to 2 hours) dropwise to the emulsifier/water slurry under high sheer (250 to 2,000 rpm, preferably at 500 to 1500 rpm) stirring. Simultaneously, water is added dropwise to the emulsion being formed. Upon completion of the silicone/lipopohilic compound mixture addition, the remaining water is added and the emulsion allowed to mix for an additional 10 minutes to an hour. The total amount of water to be added is approximately one-half of the water content of the final emulsion. Subsequently, the emulsion is diluted with water to yield a composition containing the desired amount of the aminoalkyl silicone. The composition is again subjected to high shear stirring for approximately 10 to 60 minutes, typically for about 30 minutes, to ensure proper emulsification.

It has been discovered as part of the present invention that, surprisingly, the pH of the emulsion is related to the degree of the deposition of the lipophilic compound to the teeth surface. Thus, the pH of the emulsion is preferably at least 5, more preferably from 5 to 10, and especially from 6 to 9 in order to attain optimum deposition. The optimum pH is preferably at least 7.0, e.g., 7.0-8.5. The pH of the emulsion may be adjusted with conventional acids and bases, e.g. HCl and NaOH.

The preferred oral compositions of the present invention are in the form of toothpaste creams, or gels, or measured drops. Ingredients typically included in toothpastes and gels may be used in toothpaste and gel compositions in accordance with the invention. Suitable ingredients include abrasive polishing materials, sudsing agents, flavoring agents, humectants, binders, sweetening agents, and water.

Abrasives which may be used in the compositions of the invention include alumina and hydrates thereof, such as alpha alumina trihydrate, magnesium trisilicate, magnesium carbonate, aluminosilicates, such as calcined aluminum silicate and aluminum silicate, calcium carbonate, zirconium silicate, polymethyl methacrylate, powdered polyethylene, silica xerogels, hydrogels and aerogels and the like. Also suitable as abrasive agents are calcium pyrophosphate, insoluble sodium metaphosphate, calcium carbonate, dicalcium orthophosphate, particulate hydroxyapatite and the like. Depending on the form which the oral composition is to take, the abrasive may be present in an amount of from 0 to 70% by weight, preferably 1 to 70% by weight, more preferably from 10 to 70% by weight, particularly for toothpastes.

Humectants contemplated for use in the present invention include glycerol, polyol, sorbitol, xylol, polyethylene glycols, propylene glycol, hydrogenated partially hydrolyzed polysaccharides and the like. The humectants are generally present in amounts of from 0 to 80%, preferably 5 to 70% by weight, particularly for toothpastes.

Sweeteners suitable for use in the present dentifrice, preferably at levels of about 0.1% to 5%, include saccharin.

Certain pyrophosphate and other polyphosphate salts have been disclosed in U.S. Pat. Nos. 4,515,772 and 4,627,977 as being useful as anticalculus agents. These include di- and tetra-alkali metal pyrophosphates wherein the alkali metals are preferably selected from the group consisting of sodium and potassium. Polyphosphate salts may be included generally in the amount such that it provides for at least 0.5% polyphosphate anions, the upper level being about 10%, preferably about 7.5%.

Zinc salts are disclosed as anticalculus and antiplaque agents in U.S. Pat. No. 4,100,269 and in U.S. Pat. Nos. 4,416,867, 4,425,325 and 4,339,432. Preferred compositions of the invention include zinc salts, particularly zinc citrate. The zinc compounds may be present in the compositions in amounts sufficient to furnish about 0.01% to about 4% zinc, or preferably about 0.05% to about 1%, zinc ion.

Fluoride sources used in toothpastes such as sodium fluoride, stannous fluoride, sodium monofluorophosphate, zinc ammonium fluoride, tin ammonium fluoride, calcium fluoride and cobalt ammonium fluoride may be, and preferably are, included for delivering anticaries benefit. Preferred compositions of the invention include the fluoride source. Fluoride ions are typically provided at a level of from 0 to 1500 ppm, preferably 50 to 1500 ppm, although higher levels up to about 3000 ppm may be used.

Flavors are usually included in toothpastes in low amounts, such as from 0.01 to about 5% by weight, especially from 0.1% to 5%.

Water-soluble antibacterial agents, such as chlorhexidine digluconate, quaternary ammonium antibacterial compounds and water-soluble sources of certain metal ions such as zinc, copper, silver and stannous (e.g., zinc, copper and stannous chloride, and silver nitrate) may also be included.

Titanium dioxide is a suitable whitener.

Dyes/colorants suitable for dentifrices, i.e., FD&C Blue #1, FD&C Yellow #10, FD&C Red #40, etc., may be employed in the dentifrices of the invention.

Various other optional ingredients may be included in the compositions of the invention, such as antimicrobials, antioxidants, vitamins such as vitamin C and E, other antiplaque agents such as stannous salts, copper salts, strontium salts and magnesium salts. Also included may be pH adjusting agents, anticaries agents such as urea, calcium glycerophosphate, sodium trimetaphosphate, hydrophilic silicone polymers, plant extracts, desensitizing agents for sensitive teeth such as potassium nitrate and potassium citrate, and mixtures thereof.

Ingredients mentioned above as suitable for toothpastes are generally suitable for gels, as will be apparent to one of skill in the art of toothpaste and gel formulation. Thus, except where otherwise noted, references to toothpastes are to be construed as applying to gels as well.

Typically, mouthwashes comprise a water/alcohol solution, flavor, humectant, sweetener, sudsing agent, and colorant. The corresponding compounds mentioned above which are used in toothpastes, are generally suitable within the ranges above for mouthwashes as well. The mouthwash can include ethanol at a level of from 0 to 60%, preferably from 5 to 30% by weight, however, alcohol should not be present in the amounts that would affect the stability of the emulsion.

The inventive emulsions are incorporated into dentifrice or chewing gum or lozenges compositions in the same manner as any other ingredient is incorporated in such compositions. For instance, in toothpaste preparation the emulsion is added with stirring to the main toothpaste mix. The amount of water in the emulsion is determined by the amounts of the silicone and other components. Generally, the amount is in a range of about 65% to about 99%, most preferably from about 80% to 99%. The amount of water employed in the preparation of the emulsion should not exceed the amount of water in the final composition.

According to the present invention, the lipophilic compound is deposited on the teeth surface, along with the aminoalkyl silicone, by applying the inventive compositions into an oral cavity. If the compositions are aplied by rinsing, it may be necessary to rinse repeatedly before the full beneficial effect of the compositions is realized. Thus, a particularly preferred method of applying the compositions is by brushing or chewing.

The following specific examples further illustrate the invention, but the invention is not limited thereto.

EXAMPLES

MATERIALS AND METHODS

Plaque and Calculus Inhibition

The following procedure was used to determine the inhibition of plaque growth and subsequent calculus formation after a single application of the emulsions to the glass rods.

The emulsions were applied to the first 40 mm of a 60 mm ×3 mm glass rod by brushing the rods with a soft bristle toothbrush repeatedly saturated with the test solution for 1 minute. The treated rods (triplicate samples) were rinsed with distilled water (30 seconds) and then placed into a rubber septum with a 2 mm hole (septum attached to inner surface of vial cap). These rods were subsequently introduced into a 6 dram vial containing 20 ml of growth medium with 1.0% sucrose, inoculated with $S.$ $sobrinus$ (see PLAQUE GROWTH section).

| Overnight Growth Medium Composition | |
|---|---|
| Ingredient | % |
| Trypticase Peptone | 2.000 |
| Yeast Extract | 0.500 |
| Potassium Phosphate: Monobasic | 0.160 |
| Dibasic | 0.660 |
| Sodium Chloride | 0.200 |
| Sucrose | 1.000 |
| Sodium Bicarbonate | 0.400 |
| Calcium Chloride | 0.011 |
| Magnesium Sulfate | 0.016 |
| Manganous Sulfate | 0.003 |
| Water | To 100.000 |

All samples were incubated in a 37° C. water bath for 20 hours. The plaque coated rods were then removed, immersed in sterile water (30 seconds with swirling) and placed into fresh sterile growth medium containing 0.5% sucrose. These samples were incubated for an additional 24 hours at 37° C.

To determine plaque growth or inhibition after a single emulsion application, rods containing 48 hours of plaque growth were rinsed with distilled water and later dried overnight in a vacuum dessicator over phosphorus pentoxide. Plaque accumulation was determined by the dry weight method discussed below under "PLAQUE ASSESSMENT".

To establish whether a reduction in plaque growth resulted in a reduction of calculus formation, duplicate samples of the above plaque-coated rods (48 hours) without further treatment, were mineralized in a saliva-calcifying solution as described below (see PLAQUE MINERALIZATION). Calculus formation was evaluated by determining the amount of calcium phosphate contained in the mineralized plaque (see CALCULUS ASSESSMENT).

Plaque Growth

A frozen stock culture of $S.$ $sobrinus$ 6715-14 was thawed at room temperature.

| Frozen Culture Composition | |
|---|---|
| Ingredient | % |
| Trypticase Peptone | 2.00 |
| Yeast Extract | 0.50 |
| Potassium Phosphate: Monobasic | 0.66 |
| Dibasic | 0.16 |
| Sodium Chloride | 0.20 |
| Glucose | 0.10 |

-continued

| Frozen Culture Composition | |
|---|---|
| Ingredient | % |
| Sodium Bicarbonate | 0.40 |
| Dimethyl Sulfoxide | 5.00 |
| Streptomycin Sulfate | 0.02 |
| Water | To 100.00 | a) Medium contains *S. sobrinus* (O.D. 600 nm of 0.20) 5 ml of the stock culture was added to 20 ml of seed medium contained in a 20 mm x 150 mm test tube and incubated at 37° C. for approximately 4–6 hours to yield an optical density (600 mm) of 0.35.

| Seed Medium Composition | |
|---|---|
| Ingredient | % |
| Trypticase Peptone | 2.00 |
| Yeast Extract | 0.50 |
| Potassium Phosphate: Monobasic | 0.10 |
| Dibasic | 0.40 |
| Sodium Chloride | 0.20 |
| Dextrose | 0.20 |
| Sodium Bicarbonate | 0.05 |
| Water | To 100.00 |

The content of the seed culture was then added to 1 liter of the sterile growth medium containing 1.0% sucrose (described above). After 20 minutes' mixing at room temperature to achieve homogeneity, 20 ml of inoculated medium was added to a sterile 6 dram vial containing a 60 mm × 3 mm glass rod suspended from a septum cap. All samples were incubated in a 37° C. water bath for 20 hours after which the rods were removed, immersed in sterile distilled water (30 seconds with gentle swirling) and placed into fresh sterile growth medium containing 0.5% sucrose. These samples were then incubated for an additional 24 hours at 37° C.

Plaque Mineralization

Triplicate samples of two day plaque coated rods were immersed in 20 ml of sterile distilled water for 30 seconds with gentle swirling to remove residual growth medium, then placed into the control of treatment solutions (20 ml) for 30 seconds, rinsed again with sterile water (30 seconds), placed into saliva supplemented calcifying solution (20 ml) and incubated for 6 hours at 37° C.

| Calcifying Solution Composition | |
|---|---|
| Ingredient | Concentration |
| Tromethamine (Tris) | 150.0 mM |
| Sodium Chloride | 13.0 mM |
| Potassium Chloride | 21.0 mM |
| Sodium Phosphate, Monobasic | 2.5 mM |
| Sodium Phosphate, Dibasic | 2.5 mM |
| Calcium Chloride | 1.5 mM |
| pH = 7.40 | |

The above mixture was diluted 25% with human saliva supernatant.

At the end of this time, the rods were treated again, rinsed, placed into fresh calcifying solution, and incubated for 18 hours at 37° C. This procedure of treating and placing the rods into calcifying solution twice a day (9 a.m. and 3 p.m.) was performed for 4 days. Calculus accumulation was determined as described below (See CALCULUS ASSESSMENT).

Plaque Assessment

Plaque growth and/or inhibition was evaluated by determining the total dry weight of the plaque contained on the glass rod after 48 hours growth. Dry, plaque coated rods were weighed and then stripped of deposits by placing the rods into 15 ml of 1.0N sodium hydroxide. vortexed thoroughly, and incubated at 55° C. for 2 hours. Each rod was then removed, rinsed with distilled water, dried, and re-weighed to attain a total plaque weight.

Consequently, plaque reduction was defined as:

$$\% \text{ Reduction} = \frac{\text{mg Plaque Control} - \text{mg Plaque Treatment}}{\text{mg Plaque Control}} \times 100$$

Calculus Assessment

Calculus growth and/or inhibition was determined by measuring the amount of calcium and phosphate contained in the plaque matrix after 4 days of incubation in the calcifying solution. Calcified plaque coated rods were rinsed with distilled water, and then stripped of deposits by placing the rods into 15 ml of 0.6N HCl, vortexing thoroughly, and incubating at 55° C. for 2 hours. Each sample was then filtered through a 0.80 micron nylon membrane and the filtrate analyzed for total calcium by atomic absorption and for phosphorus by the Chen method (Chen et al., "Microdetermination of Phosphorus", Anal. Chem., 28, 1756–1758 (1956)). The calcium and phosphorus values were converted to milligrams of calcium and phosphorus or simply totaled as milligrams of calcium phosphate. Consequently, calculus inhibition was defined as:

$$\% \text{ Inhibition} = \frac{\text{mg CaPO}_4 \text{ Control} - \text{mg CaPO}_4 \text{ Treated Plaque}}{\text{mg CaPO}_4 \text{ Control}} \times 100$$

Thymol Assessment

A colorimetric assay (as described by Lacoste et al., Anal. Chem., 31, 1246–1249 (1959)) was used to determine the amount of thymol deposited on glass rods. Rods brushed (1 minute) with silicone/thymol emulsions were stripped of deposits by soaking the treated rods in 10 ml of a solution containing 3 parts of 95% ethanol and 1 part 2N KOH for 1 hour at room temperature. Two ml of this stripping solution was then added to 5 ml of 0.4M boric acid - 0.1N NaOH buffer (pH 9.2) followed by the addition of 0.1 ml of aminoantipyrine (5.0% solution). After vortexing the mixture (30 seconds), 0.1 ml of potassium ferricyanide solution (10.0% was added to the sample, vortexed, and allowed to sit at room temperature for 15 minutes. The absorbance of each sample (in triplicate) was determined at 500 nm and compared to a thymol standard curve prepared with 95% ethanol as the solvent. The aminoalkyl silicone did not interfere with the colorimetric reaction.

EXAMPLE 1

Effect of Thymol Concentration on Plaque/Calculus Formation

Emulsion Preparation

The oil-in-water emulsions were prepared containing 1.0% aminoalkyl silicone of Formula 5 and various levels of a lipophilic compound (thymol), and 0.35% of cocoalkyldimethyl amine oxide emulsifier. The emulsions were prepared as follows.

The appropriate amounts of thymol were added to the aminoalkyl silicone at 60° C. This mixture was stirred using a stirring bar until complete dissolution of the lipophilic compound occurred (approximately 10 minutes). The amine oxide was dissolved in distilled water with moderate stirring, using an overhead mixer with a 3 cm diameter stir blade. The aminoalkyl silicone/thymol mixture, at room temperature, was then slowly added, over a period of 10 minutes to the amine oxide solution with high shear stirring (1000 rpm) using an overhead stirrer, until a visibly stable emulsion was formed. The emulsion was subsequently diluted with water to yield an emulsion containing 1.0% silicone. This preparation was again subjected to high shear stirring for approximately 30 minutes to ensure proper emulsification. The pH of all the emulsions was 8.0. The emulsions were brushed on glass rods for 1 minute. Thymol deposition, % plaque inhibition and % calculus inhibition were measured. The following results were obtained.

| % Thymol | μg Thymol Deposited | % Inhibition Plaque | Calculus |
|---|---|---|---|
| 0.00 | 0 | 2 | 0 |
| 0.10 | 82 | 7 | 8 |
| 0.20 | 130 | 23 | 12 |
| 0.25 | 155 | 60 | 21 |
| 0.30 | 196 | 78 | 47 |
| 0.40 | 215 | 80 | 50 |

The example illustrates that the aminoalkyl silicone carrier effectively deposited thymol on the rods, and that increasing levels of thymol produced concomitant reductions in plaque and calculus. Maximum thymol deposition and antiplaque/anticalculus activities were obtained with an aminoalkyl silicone emulsion containing 0.30–0.40% thymol. These preparations, depositing 196–215 μg thymol, reduced plaque by 78–80%, which, in turn, provided a 47–50% reduction in calculus after mineralizing in plaque for 4 days in a calcifying solution without further treatment. In other words, this result was achieved after treating the glass rods only once (prior to plaque growth) throughout the entire experiment.

Experiments (controls) were also carried out with thymol solutions alone (0.10–0.40% in 25% ethanol), and 1.0% aminoalkyl silicone solutions without thymol, and amine oxide solutions (0.35%) without either thymol or aminoalkyl silicone. Thymol solutions alone without an aminoalkyl silicone did not deposit thymol, and, as a result, no reduction in plaque/calculus was observed. Similar results were obtained with other controls. The data demonstrate that an oil phase containing both an aminoalkyl silicone and a lipophilic compound is required for delivering and enhancing the deposition of the lipophilic compound on the teeth surface.

EXAMPLE 2

Oil-in-water emulsions containing aminoalkyl silicone of Formula 5 (1%), amine oxide (emulsifier) and various lipophilic antimicrobial agents as indicated in the table below, were prepared (as in Example 1). % plaque reduction was evaluated. The results that were obtained are summarized as follows:

| Emulsion | % Plaque Reduction |
|---|---|
| 1% silicone; 0.3% thymol; 0.35% emulsifier | 80 |
| 1% silicone; 0.3% menthol; 0.35% emulsifier | 7 |
| 1% silicone; 0.3% eucalyptol; 0.35% emulsifier | 5 |
| 2% silicone; 0.5% triclosan; 0.7% emulsifier | 28 |

For every emulsion composition listed above, two control experiments were carried out: an aminoalkyl silicone without an antimicrobial and an antimicrobial agent without an aminoalkyl silicone. All control experiments resulted in 0% plaque reduction. The example demonstrates that an oil phase containing both an aminoalkyl silicone and a lipophilic compound is required for delivering and imparting the lipophilic compound to the teeth surface.

EXAMPLE 3

The following emulsions were prepared by the procedure of Example 1. All emulsions contained 1% aminoalkyl silicone of Formula 5. The pH of each emulsion was 8.0. The emulsions were brushed on glass rods for 1 minute. Thymol deposition and % plaque reduction were evaluated. The following results were obtained.

| Effect of Emulsion Stability on Antiplaque Activity of Aminoalkyl Silicone/Thymol Emulsions | | | |
|---|---|---|---|
| % Amine Oxide | μg Thymol Deposited | Stability | % Plaque Reduction |
| 0.35 | 183 | 1-3 weeks | 78 |
| 0.50 | 131 | about one month | 55 |
| 0.70 | 91 | microemulsion | 10 |
| 1.00 | 90 | microemulsion | 6 |

This Example illustrates that emulsion stability and deposition of the lipophilic compound are interrelated. Formation of a microemulsion (stable up to about 3 months at room temperature) reduced thymol deposition which, in turn, diminished antiplaque activity.

EXAMPLE 4

Effect of pH on Antiplaque Activity of Aminoalkyl Silicone/Thymol Emulsions

Emulsions were prepared (as in Example 1) containing 1.0% aminoalkyl silicone, 0.35% amine oxide, 0.30% thymol. The pH of the emulsion was varied by adding in HCl or in NaOH. The emulsions were brushed on glass rods for 1 minute. Thymol deposition and % plaque reduction were evaluated. The following results were obtained.

| Emulsion pH | μg Thymol Deposited | % Plaque Reduction |
|---|---|---|
| 5.0 | 74 | 6 |
| 6.0 | 104 | 15 |
| 7.0 | 125 | 17 |
| 8.0 | 195 | 84 |
| 8.5 | 195 | 83 |

This example illustrates that the pH of the emulsion of at least 5.0, and particularly at least 7.0, enhances thymol deposition, resulting in increased plaque reduction benefit.

EXAMPLE 5

Effect of Gum Thickener on Antiplaque Activity of Aminoalkyl Silicone/Thymol Emulsions Emulsions were prepared (as in Example 1) containing 1.0% aminoalkyl silicone, 0.35% amine oxide, 0.30% thymol. The emulsions also contained varying amounts of gum, Natrosol 250H ® (ex Hercules). The gum was added to the final emulsion: incremental portions of the gum were added slowly with stirring to prevent clumping. The stirring was conducted with an overhead stirrer at a moderate shear of 250–500 rpm. The pH of each emulsion was 8.0. The emulsions were brushed on glass rods for 1 minute. Thymol deposition and % plaque reduction were evaluated. The following results were obtained.

| % Gum | μg Thymol Deposited | % Plaque Reduction |
|---|---|---|
| 0.00 | 185 | 80 |
| 0.10 | 192 | 81 |
| 0.20 | 186 | 78 |

This example illustrates that the addition of gum to the emulsions is effective. The gum did not reduce the thymol deposition or plaque reduction benefit. In addition, the gum prevented emulsion separation for three months.

EXAMPLE 6

The solubility of several lipophilic agents in aminoalkyl silicone was ascertained, as follows:

10 grams of the aminoalkyl silicone of Formula 5 were heated, while stirring with a magnetic stirrer, to about 60° C. An amount (as indicated in the table) of a lipophilic compound was added with stirring to the heated silicone. The resulting mixture was maintained at about 60° C. for about 10 minutes. The results that were obtained are summarized as follows:

| Lipophilic Compound | Amount Soluble in 10 g of Aminoalkyl silicone |
|---|---|
| Thymol | 5.0 grams |
| Phenol | 3.0 grams |
| Hexylresorcinol | 1.0 gram |
| Benzoic Acid | 1.0 gram |
| Methyl Paraben | 1.5 grams |
| Propyl Paraben | 2.2 grams |
| Peppermint Oil | 1.0 gram |
| Spearmint Oil | 1.0 gram |
| Cinnamon Leaf Oil | 1.0 gram |
| Oregano Oil | 1.0 gram |
| Bay Leaf Oil | 1.0 gram |

The Example illustrates that the solubility of a lipophilic compound in an aminoalkyl silicone is easily ascertained and that all the lipophilic compounds in the above table would be suitable for incorporation in the emulsions within the scope of the invention.

EXAMPLE 7

Emulsions containing 1.0% of aminoalkyl silicone, thymol and various emulsifiers were prepared as follows:

20.0 grams of silicone was heated to 60 C. in a water bath to which 6.0 grams of thymol was added and dissolved. Using an overhead mixer, 2.96 grams of Tergitol NP-10 ®, 0.98 grams of Tergitol NP-15 ® and 3.64 grams of water were mixed into a slurry paste. The silicone/thymol mixture was slowly added dropwise over a 30 minute period to the surfactant/water phase under high shear (1000 rpms) stirring. Simultaneously, water was added dropwise to the emulsion being formed. The total amount of water to be added was 23.56 grams; approximately one half of this volume was added during the silicone addition. Upon completion of the addition of the silicone/thymol, the remaining water was added and the emulsion allowed to mix for an additional 15 minutes. The total weight of the emulsion was 57.14 grams yielding a 35% silicone emulsion. 2.86 grams of this emulsion was added to 97.14 grams of water and mixed for 15 minutes under high shear stirring. This yielded an emulsion containing 1.0% silicone and 0.3% thymol.

For the preparation of an emulsion containing Pluronic, 3.92 grams of Pluronic P-85 ® was used. The remaining procedure was the same.

Thymol deposition of the resulting emulsions was evaluated. The results that were obtained are summarized as follows:

| % Thymol | Surfactant Type | % Surfactant | μg Thymol Deposited |
|---|---|---|---|
| 0.30 | Amine Oxide | 0.35 | 173 |
| 0.15 | Pluronic[1] | 0.20 | 61 |
| 0.30 | Pluronic[1] | 0.20 | 90 |
| 0.15 | Tergitol[2] | 0.20 | 44 |
| 0.30 | Tergitol[2] | 0.20 | 213 |

[1]Pluronic P-85 ® (BASF)
[2]A mixture of Tergitol NP-10 ® and Tergitol NP-15 ® (Union Carbide)

EXAMPLE 8

A typical toothpaste formulation incorporating the oil-in-water emulsion according to the present invention is as follows:

| INGREDIENT | % W/W |
|---|---|
| Aminoalkyl Silicone | 1.00 |
| Thymol | 0.30 |
| Aromox DMMC-W ® (30% Cocoalkyl Dimethyl Amine Oxide) | 0.35 |
| Natrosol 250-H ® | 1.00 |
| Silica 63x | 26.00 |
| Silica 244 | 11.40 |
| Titanium Dioxide | 0.50 |
| Sodium Fluoride | 0.20 |
| Sodium Saccharin | 0.20 |
| Flavor | 1.00 |
| Glycerin | 29.00 |
| Water | 29.05 |
| TOTAL | 100.00 |

EXAMPLE 9

Effect of the Emulsions on Plaque Mineralization In-Vitro Microbial Mineralization Model

| Treatment | % Calculus Reduction |
|---|---|
| Distilled Water | — |
| 0.35% Amine Oxide | 8 |
| 0.30% Thymol | 10 |
| 1.0% Silicone/0.35% Amine Oxide | 0 |

| Treatment | % Calculus Reduction |
|---|---|
| 1.0% Silicone/0.35% Amine Oxide/0.3% Thymol | 0 |

(a) 4 day plaque mineralization
(b) Plaque coated rods treated for 2 minutes with agents
(c) Thymol dissolved in 25% ethanol In contrast to the previous examples, the emulsion was not brushed onto the rods prior to the initiation of plaque growth. The results show that calculus reduction benefit was less significant. The results appear to be related to the dip method used to apply the treatment solutions. It appears that simply immersing the calcified plaque into the emulsions is not as effective as brushing for delivering the aminoalkyl silicone/lipophilic compound emulsion to the surface. When rinsing is used instead of brushing in order to apply the solutions, repeated rinsing treatments may be recommended.

EXAMPLE 10

Effect of Aminoalkyl Silicone/Thymol Emulsions on Calculus Formation in Rat Model

| Treatment | % Calculus Reduction |
|---|---|
| 1.50% EHDP (a) | 37 |
| 1.75% Amine Oxide | 15 |
| 5.0% Silicone + 1.75% Amine Oxide | 0 |
| 5.0% Silicone + 1.75% Amine Oxide + 1.50% Thymol | 3 |

(a) Ethanehydroxydiphosphonate: Positive Control - a known anticalculus agent.

A cotton swab was used to apply the treatment solutions. This Example, like Example 9, appears to demonstrate that the calculus reduction benefit is less significant when rinsing or dipping is employed to apply the composition into an oral cavity.

Supplies not mentioned in the examples are as follows:

| Ingredient | Tradename | Supplier |
|---|---|---|
| Thymol | | Sigma Chemical |
| Menthol | | " |
| Eucalyptol | | " |
| Triclosan | Irgasan DP300 ® | Ciba-Geigy |
| Amine Oxide (cocoalkyl dimethyl amine oxide) | Aromox DMMC-W ® | AKZO |
| Silica 63X | Syloid 63x ® | W. R. Grace |
| Silica 244 | Syloid 244 ® | " |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. An oral composition comprising an oil-in-water emulsion comprising:
   (a) an oil phase comprising a noncyclic, hydrophobic aminoalkyl silicone and an orally acceptable lipophilic compound, the lipophilic compound being soluble in the aminoalkyl silicone and selected from the group consisting of an antimicrobial compound, a flavorant and mixtures thereof; and
   (b) an aqueous phase comprising an emulsifier, wherein the aminoalkyl silicone is employed in the amount effective to form a hydrophobic layer on the teeth surface and the lipophilic compound is present in an amount to provide a benefit selected from the group consisting of plaque and/or calculus formation inhibition, prolonged flavor perception, malodor masking benefit, sustained breath refreshing benefit and combinations thereof
wherein the aminoalkylsilicone is comprised of two basic units:
   (1) $(R^1)_m\text{---}(R)_n\text{---}SiO_{(4-m-n)/2}$ wherein m+n is 1, 2 or 3; n is 1, 2, or 3; m is 0, 1, or 2; and
   (2) $(R^1)_a(R^2)_b SiO_{(4-a-b)/2}$ wherein a+b is 1, 2, or 3, and a and b are integers
wherein $R^1$ and $R^2$ are hydrocarbons or fluorinated hydrocarbons of 1 to 10 carbons, hydroxyl, alkoxyl, hydrogen or acetoxy, and R is

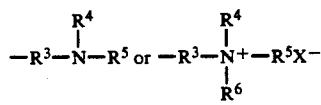

wherein $R^3$ is a divalent alkylene of 1–20 carbon atoms or a hydrocarbon of 1–20 carbon atoms containing oxygen atoms, $R^4$, $R^5$ and $R^6$ may be different or the same and are selected from the group consisting of H, hydrocarbons of 1–20 carbons, and hydrocarbons of 1–20 carbons containing N and/or O atoms, and $X^-$ is a monovalent anion, said aminoalkyl silicone including 60% or fewer by repeat unit of unit (1).

2. The composition of claim 1 wherein the aminoalkyl silicone has a molecular weight of at least 5,000.

3. The composition of claim 1 wherein the aminoalkyl silicone has a molecular weight from 5,000 to 100,000.

4. The composition of claim 1 wherein $R^1$ is -methyl, -ethyl, -phenyl, -vinyl, trifluoropropyl or -cyano.

5. The composition of claim 1 wherein $R^2$ is -methyl, -ethyl, -phenyl, -vinyl, trifluoropropyl or -cyano.

6. The composition of claim 1 wherein $R^3$ is a divalent alkylene having from 3 to 5 carbon atoms.

7. The composition of claim 1 wherein R is selected from the group consisting of:

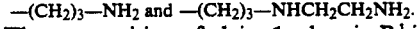

8. The composition of claim 1 wherein $R^1$ is selected from the group consisting of:

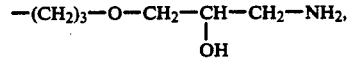

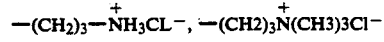

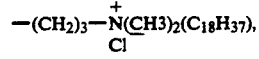

and

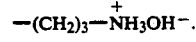

9. The composition of claim 1 wherein the lipophilic compound is a flavorant selected from the group consisting of wintergreen oil, oregano oil, hay leaf oil, peppermint oil, spearmint oil, clove oil, sage oil, sassafras oil, lemon oil, orange oil, anise oil, benzaldehyde, bitter almond oil, camphor, cedar leaf oil, marjoram oil, citronella oil, lavendar oil, mustard oil, pine oil, pine needle oil, rosemary oil, thyme oil, cinnamon leaf oil, and mixtures thereof.

10. The composition of claim 1 wherein the lipophilic compound is the antimicrobial compound.

11. The composition of claim 10 wherein the antimicrobial compound is selected from the group consisting of thymol, menthol, triclosan, 4-hexylresorcinol, phenol, eucalyptol, benzoic acid, benzoyl peroxide, butyl paraben, methyl paraben, propyl paraben, salicylamides, and mixtures thereof.

12. The composition of claim 1 wherein the pH of the composition is at least 5.0.

13. The composition of claim 1 wherein the pH of the composition is at least 7.0.

14. The composition of claim 1 wherein the emulsifier is selected from the group consisting of a nonionio emulsifier, a cationic emulsifier, and mixtures thereof.

15. The composition of claim 14 wherein the emulsifier is the nonionic emulsifier.

16. The composition of claim 15 wherein the nonionic emulsifier is amine oxide.

17. The composition of claim 1 wherein the composition comprises from about 0.1% to about 20% of the aminoalkyl silicone and from about 0.01% to about 10% of the lipophilic compound.

18. The composition of claim 1 wherein the amount of the emulsifier is from about 0.05% to about 10%.

19. The composition of claim 1 wherein the composition further comprises a source of fluoride ion.

20. The composition of claim 1 wherein the composition further comprises a source of zinc ion.

21. A method of delivering a lipophilic compound to the teeth surface comprising applying into oral cavity the composition of claim 1.

22. The method of claim 21 wherein the composition is applied by brushing or chewing.

23. The method of claim 21 wherein the composition is applied separately from a regular dentifrice treatment.

24. A process of preparing an oral composition comprising an oil-in-water emulsion, the process comprising the steps of:
(a) preparing a mixture comprising an aminoalkyl silicone and a lipophilic compound to obtain an oil phase;
(b) preparing an aqueous phase comprising an emulsifier;
(c) adding the oil phase to an aqueous phase, with stirring, to obtain the oil-in-water emulsion; and
wherein the aminoalkyl silicone is comprised of two basic units:
(1) $(R^1)_m$—$(R)_n$—$SiO_{(4-m-n)/2}$ wherein m+n is 1, 2 or 3; n is 1, 2, or 3; m is 0, 1, or 2; and
(2) $(R^1)_a(R^2)_b SiO_{(4-a-b)/2}$ wherein a+b is 1, 2, or 3, and a and b are integers
wherein $R^1$ and $R^2$ are hydrocarbons or fluorinated hydrocarbons of 1 to 10 carbons, hydroxyl, alkoxyl, hydrogen or acetoxy, and R is

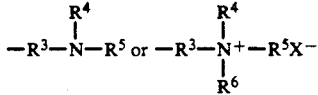

wherein $R^3$ is a divalent alkylene of 1–20 carbon atoms or a hydrocarbon of 1–20 carbon atoms containing oxygen atoms, $R^4$, $R^5$ and $R^6$ may be different or the same and are selected from the group consisting of H, hydrocarbons of 1–20 carbons, and hydrocarbons of 1–20 carbons containing N and/or O atoms, and $X^-$ is a monovalent anion, said aminoalkyl silicone including 60% or fewer by repeat unit of unit (1) and the lipophilic compound is selected from the group consisting of an antimicrobial compound, a flavorant and mixtures thereof, wherein, the aminoalkyl silicone is present in an amount effective to form a hydrophobic layer on teeth surfaces and the lipophilic compound is present in an amount to provide a benefit selected from the group consisting of plaque and/or calculus formation inhibition, prolonged flavor perception, malodor masking benefit, sustained breath refreshing benefit and combinations thereof.

* * * * *